(12) United States Patent
Schneider et al.

(10) Patent No.: US 8,275,184 B2
(45) Date of Patent: Sep. 25, 2012

(54) MEASURING BODY FOR AN IMPLANT AND METHOD FOR PROVIDING A 3D MEASUREMENT DRAWING

(75) Inventors: Sascha Schneider, Muhltal (DE); Frank Weber, Hemsbach (DE)

(73) Assignee: Sirona Dental Systems GmbH, Bensheim (DE)

( * ) Notice: Subject to any disclaimer, the term of this patent is extended or adjusted under 35 U.S.C. 154(b) by 154 days.

(21) Appl. No.: 12/785,282

(22) Filed: May 21, 2010

(65) Prior Publication Data
US 2010/0296710 A1 Nov. 25, 2010

Related U.S. Application Data

(63) Continuation of application No. PCT/EP2008/066044, filed on Nov. 21, 2008.

(30) Foreign Application Priority Data

Nov. 23, 2007 (DE) .......................... 10 2007 056 820

(51) Int. Cl.
*G06K 9/00* (2006.01)

(52) U.S. Cl. ....................................... 382/128; 382/154

(58) Field of Classification Search .................. 382/128, 382/154, 132; 433/173, 72, 191, 193; 700/95, 700/97, 98
See application file for complete search history.

(56) References Cited

U.S. PATENT DOCUMENTS

| 5,401,170 | A | | 3/1995 | Nonomura | |
|---|---|---|---|---|---|
| 5,857,853 | A | * | 1/1999 | van Nifterick et al. | 433/213 |
| 6,287,119 | B1 | | 9/2001 | van Nifterick et al. | |
| 6,558,162 | B1 | * | 5/2003 | Porter et al. | 433/173 |
| 6,788,986 | B1 | * | 9/2004 | Traber et al. | 700/98 |
| 6,925,198 | B2 | * | 8/2005 | Scharlack et al. | 382/128 |
| 2006/0019219 | A1 | * | 1/2006 | Saliger et al. | 433/173 |
| 2008/0206710 | A1 | | 8/2008 | Kruth et al. | |

FOREIGN PATENT DOCUMENTS

| DE | 694 13 852 T2 | 6/1999 |
|---|---|---|
| DE | 10 2004 035 091 A1 | 2/2006 |
| DE | 600 30 465 T2 | 12/2006 |
| EP | 0 599 578 A2 | 6/1994 |
| EP | 1 062 916 B1 | 12/2000 |
| WO | 2006/079188 A1 | 8/2006 |

OTHER PUBLICATIONS

International Search Report dated May 13, 2009.

* cited by examiner

*Primary Examiner* — Chan S Park
*Assistant Examiner* — Nancy Bitar
(74) *Attorney, Agent, or Firm* — Fitzpatrick, Cella, Harper & Scinto

(57) ABSTRACT

A measuring body for an implant, having a measuring geometry that can be captured by a measuring camera and a connection geometry on the implant. Said measuring geometry is arranged on a test part and the connection geometry is arranged on a bearing part, both parts being embodied as separate components. Said bearing part comprises a bearing for the test part and the test part comprises a counter bearing to the bearing and the measuring geometry is provided on a free end of the test part. Also provided is a method for capturing a 3D-measurement drawing of a measuring body that is arranged on an implant.

14 Claims, 3 Drawing Sheets

MEASURING BODY FOR AN IMPLANT AND METHOD FOR PROVIDING A 3D MEASUREMENT DRAWING

CROSS REFERENCE TO RELATED APPLICATIONS

This application is a continuation of International Application No. PCT/EP2008/066044, filed Nov. 21, 2008, which in turn claims the benefit of priority based on German Patent Application No. 10 2007 056820.9, filed Nov. 23, 2007, each of which is incorporated by reference herein in its entirety, as if set forth fully herein. International Application No. PCT/EP2008/066044 has been published in German, but not English, as International Publication No. WO 2009/065954 A1, on May 28, 2009.

BACKGROUND OF THE INVENTION

The invention relates to a measuring body for an implant, comprising a measuring geometry detectable by a scanning camera and a connecting geometry for the implant.

The invention further relates to a method for generating a measured 3D image of a measuring body mounted on an implant, and the implant to be used is selected from a number of various types of implant.

In the case of CAD/CAM assisted provision of jaw implants, a freshly inserted or already healed implant is fitted with a temporary measuring body to indicate the orientation and position of the implant at a level above the region of the jaw or gingiva. This method is also used for implant analogs placed in plaster models. With the aid of a surface scan of the situation it is possible, by means of special algorithms, to recognize the exposed shape of the measuring body automatically and to compute its orientation and position. Since its geometrical shape is precisely known, the orientation of the implant and its position can be computed that are hidden in the jaw, in the gingiva, or in the model and are not directly visible in a surface scan of the situation. It is then possible to design an appropriate dental prosthetic item by means of CAD/CAM.

A large number of greatly varying implant shapes are available on the market, these differing, inter alia, mainly in the diameter and connecting geometry of the mounted dental prosthetic item, for example an abutment.

Hitherto, a completely new, single-piece measuring body has been fabricated for each required implant shape. Some manufacturers use extended screws in the implant for this purpose. Although it has hitherto been possible to keep the upper part of the body in most cases geometrically identical, it has still had to be freshly fabricated together with the fixed bottom part of the measuring body, for example using an injection mold. Each fresh measuring body has required a separate individual fabrication process. In such cases it has been necessary to create individual patterns in elaborate production steps and these have had to be measured for accuracy until the required fit was achieved. There is thus the risk that, even when the top part retains the same geometrical shape, there will nevertheless be slight unintentional dimensional discrepancies depending on the mold used. The production and completion of the whole part are the responsibility of the developer of the CAD/CAM dental software for finding the measuring body in the surface scan and then producing a tooth restoration.

PRIOR ART

Measuring bodies are disclosed in DE 694 13 852 T2. The measuring bodies are formed as a single piece and exhibit a shaft, at one end of which the measuring geometry is disposed and at its other end there is provided a spigot, by means of which the measuring body is fitted to the implant.

EP 0 599 578 A2 discloses a measuring body with a measuring geometry and an auxiliary measuring body which is attachable to the main measuring body. When measurement within the mouth is not possible, the auxiliary measuring body is mounted on the main measuring body so that the auxiliary measuring body forms the inspection part and can be recorded by the impression compound subsequently introduced. The auxiliary measuring body has a measuring geometry on its underside projecting from the impression compound so that the position and alignment of the auxiliary measuring body within the impression can be determined. No provision is made for measurement of the auxiliary body mounted on the implant.

Furthermore, DE 10 2004 035 091 A1 discloses measuring elements having a measuring geometry and provided with a connecting geometry for the implant. The measuring elements are fixed via the connecting geometry to the implant so that the alignment of the implant axis on the one hand and the position of the connecting geometry on the other hand can be deduced from the measuring geometry.

It is an object of the invention to design and configure a measuring body such that reduced manufacturing costs are incurred.

SUMMARY OF THE INVENTION

According to the Invention, the measuring geometry is disposed on an inspection part and the connecting geometry on a supporting member and both the inspection part and the supporting member are in the form of separate components, and the supporting member has a bearing for the inspection part and the inspection part has a counter-bearing matching said bearing and the measuring geometry is provided on a free end of the inspection part mounted on said supporting member.

When the inspection part is in the mounted state, the measuring geometry faces the scanning camera. This means that the inspection part can be developed and fabricated independently of the supporting member. In the case of varying types of implant, it is necessary to appropriately redesign and re-make the supporting member. This can take place, according to the invention, irrespectively of designing or fabricating the inspection part. The design of the inspection part substantially depends on the measuring geometry and the evaluation software developed for this purpose, which can remain unchanged despite adaptation of the measuring body to new types of implant by modification of the supporting member.

The development effort for the software when adding new implant shapes for support thereby is reduced. Furthermore, alteration of the inspection part, for example, for the purpose of improving software-assisted position finding, has no influence on the supporting member.

The provision of a separate inspection part reduces the development effort for the hardware, that is to say, for the overall measuring body. Since the measuring body is a precision-made part which has to be fabricated to a tolerance of a few μm, the development effort for the production of a mold or of a machine adapted for fabrication of the inspection part of the measuring body occurs only once. Only the supporting member must be redeveloped and re-made for each new implant shape to be supported.

It is also possible to evade the fabrication of the supporting member by relaying the geometrical fitting requirements of the inspection part to other connecting geometries. Thus, for example, the inspection part can be produced, and the associated surface recognition algorithm developed by the software developer, while the supporting member is manufactured by the producer of the respective implant shape. Another advantage consists in that the supporting member of the measuring body can be composed of an arbitrary material when used in the mouth of a patient, that is, for example, a food-grade material, whilst the inspection part can be formed from a readily scannable material. Thus it is possible, for example, to employ the supporting member a number of times using disinfectable materials.

The invention makes it possible, as explained above, to simplify and segregate the sequence of operations required for the production of a new measuring body for detection of the position and orientation of an implant placed in the jawbone. The software-based and hardware-(tool)-based development costs are both reduced.

Advantageously, the bearing has a longitudinal axis and a first stop limit surface effective in the direction of the longitudinal axis and the counter-bearing has a longitudinal axis and a second stop limit surface effective in the direction of said longitudinal axis, and the first stop limit surface and the second stop limit surface can be caused to abut each other in the axial direction of the longitudinal axes. The stop limit surfaces can preferably be normal to the longitudinal axis such that radial contact between the bearing and the counter-bearing does not come about via the stop limit surfaces. In addition to the stop limit surfaces, other guide surfaces parallel to the longitudinal axis can be provided to ensure radial guidance between the bearing and the counter-bearing.

It may also be advantageous when the supporting member exhibits a connecting geometry which corresponds to the connecting geometry of the implant. It is usually desirable to connect the measuring body to the connecting geometry of the implant, in order not only to detect the axial alignment of the implant but also to register the angular position of the connecting geometry of the implant.

It may also be advantageous when the bearing and the counter-bearing have orienting means to ensure perfect orientation in the circumferential direction relative to the longitudinal axes between the supporting member and the inspection part. With alignment of the supporting member toward the connecting geometry of the implant it can now be advantageous to transmit the position of the inspection part relative to the supporting member at least in the circumferential direction unambiguously via the aforementioned orienting means.

On the other hand it may be advantageous for the orienting means to be in the form of stop means or stop limit surfaces and to form an anti-twist stop with reference to the longitudinal axes and for the orienting means of the bearing to be in the form of a groove and the orienting means of the counter-bearing to be in the form of a projection, while the groove and the projection can be caused to interconnect in the circumferential direction to form an anti-twist stop. The formation of the stop means as a groove and a projection or tongue can be a simple variant of possible stop means. The projection or tongue need not extend over the entire length of the groove. It can suffice if the projection extends only over a portion of the length of the bearing so that the connection between the bearing and the counter-bearing with reference to the interacting surfaces can be effected stepwise.

Furthermore, it can be of advantage to adapt the bearing and the counter-bearing so as to be interplugged, the bearing being in the form of a cylinder and the counter-bearing in the form of a piston. The piston can thus be pushed into the cylinder in a simple manner. By this means at least radial guidance between the bearing and counter-bearing is ensured.

The aforementioned orienting means, for example the groove and the projection, can serve as stop means for alignment in the circumferential direction. The first and second stop limit surfaces can define the remaining final degree of freedom in the axial direction so that in all a five-point bearing between the inspection part and the supporting member is provided.

It may also be advantageous when the connecting geometry of the measuring body incorporates a spigot adapted to engage a depression in the implant. The spigot can transfer the axial alignment of the implant to the supporting member. The remaining part of the connecting geometry can mainly serve to transfer the position data of the implant relating to its axial height and angular position with reference to the longitudinal axis.

It may also be advantageous when the inspection part and the supporting member are, after joining, irremovably connected to each other. The supporting member and the inspection part can then be independently developed and fabricated, and finally, the measuring body can be converted to a single entity by combining the two parts by, say, a mechanical forcing, plugging, or injecting mechanism.

Another object of the invention relates to a method for generating a measured 3D image of a measuring body disposed on an implant. The method of the invention involves the use of a measuring body as described above, and the implant to be used is selected from a number of various types of implant. On the implant there is mounted a supporting member matching the type of implant used. A standardized inspection part fabricated independently of the supporting member is connected to the supporting member and placed in the implant, and then the measuring geometry of the mounted inspection part is imaged by means of the scanning camera.

According to an alternative invention, it is possible to first place the inspection part on the supporting member matching the type of implant and then to place the resulting measuring body on the implant, after which the measuring geometry of the inspection part is imaged, in the mounted state, by means of the camera.

In this context it may be of advantage when the inspection part is aligned by the orienting means relatively to the supporting member in the circumferential direction about the longitudinal axis. In this case the angular position of the implant, as has been communicated to the supporting member via the connecting geometry and from the supporting member to the inspection part, can thus be registered by the scanning camera.

Furthermore it can be of advantage for the supporting member to be aligned relatively to the implant in the circumferential direction with respect to the longitudinal axis by means of the connecting geometry.

Likewise, it can be of advantage when the first stop limit surface and the second stop limit surface are moved together in the direction of the longitudinal axis so as to abut each other.

BRIEF DESCRIPTION OF THE DRAWINGS

Exemplary embodiments of the invention are illustrated in the drawings, in which.

Figure 1:
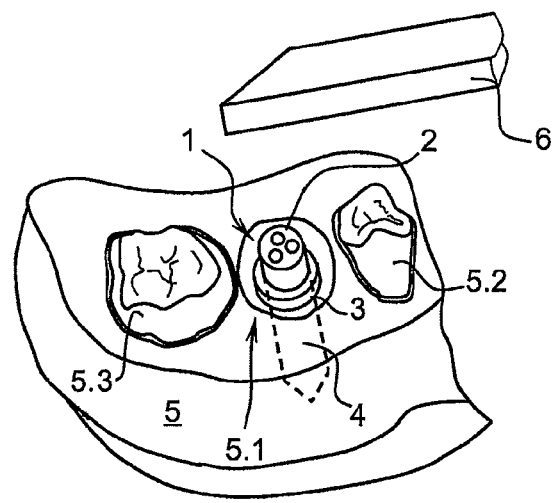
FIG. 1 is a section of a jaw model including a restoration site and two adjacent teeth.

A measuring body 1 comprising an inspection part 2 and a supporting member 3, is in position on an implant 4 screwed into a model of a jaw 5 at a restoration site. The inspection part 2 has a measuring geometry 2.5 as shown in FIG. 2, which measuring geometry is recorded by a scanning camera 6 held above the model.

Figure 2:
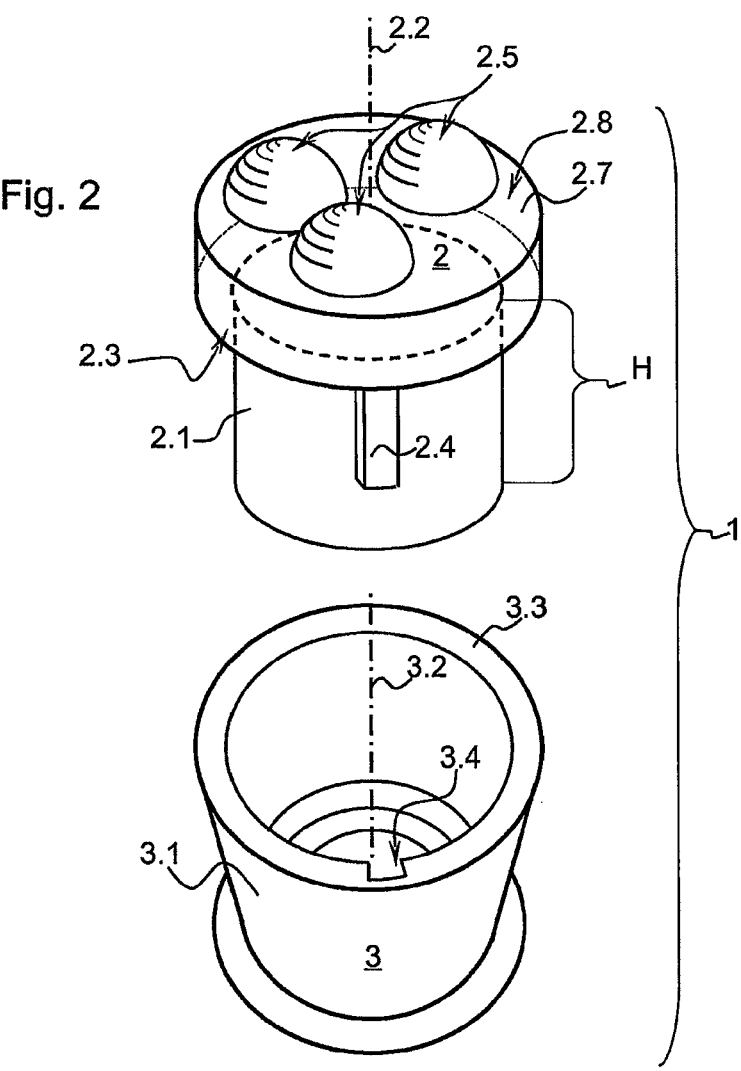
FIG. 2 is a perspective illustration of the measuring body.

The measuring body 1 illustrated in FIG. 2 comprises the supporting member 3, into which the inspection part 2 can be inserted. The supporting member 3 has a bearing 3.1 in the form of a cylinder. The inspection part 2 has a counter-bearing 2.1 in the form of a piston which can be inserted in the cylinder 3.1. Both the piston 2.1 and the cylinder 3.1 have a longitudinal axis 2.2, 3.2, which axes run coaxially to each other in the inserted state. The inspection part 2 has the measuring geometry 2.5 on its end opposing the bearing 2.1, which measuring geometry consists of three semispherical partial geometries disposed on an end face 2.8. A head 2.7 of the inspection part 2 has a diameter greater than that of the piston 2.1. The transition area between the head 2.7 and the piston 2.1 is in the form of a second stop limit surface 2.3 which, in the inserted state, can be brought to bear against an end-face first stop limit surface 3.3 of the cylinder 3.1.

Both the piston 2.1 and the cylinder 3.1 exhibit orienting means 2.4, 3.4. The orienting means 2.4 of the piston 2.1 is in the form of a projection, while the orienting means 3.4 of the cylinder 3.1 is in the form of a groove to form a tongue and groove connection. The projection 2.4 extends over only part of the height H of the piston 2.1 such that the piston 2.1 can first of all be inserted into the cylinder 3.1 and can only then, by aligning the piston 2.1 and cylinder 3.1 in the circumferential direction relative to the longitudinal axis 2.2, 3.2, be pushed in causing contact between the orienting means 2.4, 3.4.

Figure 3:
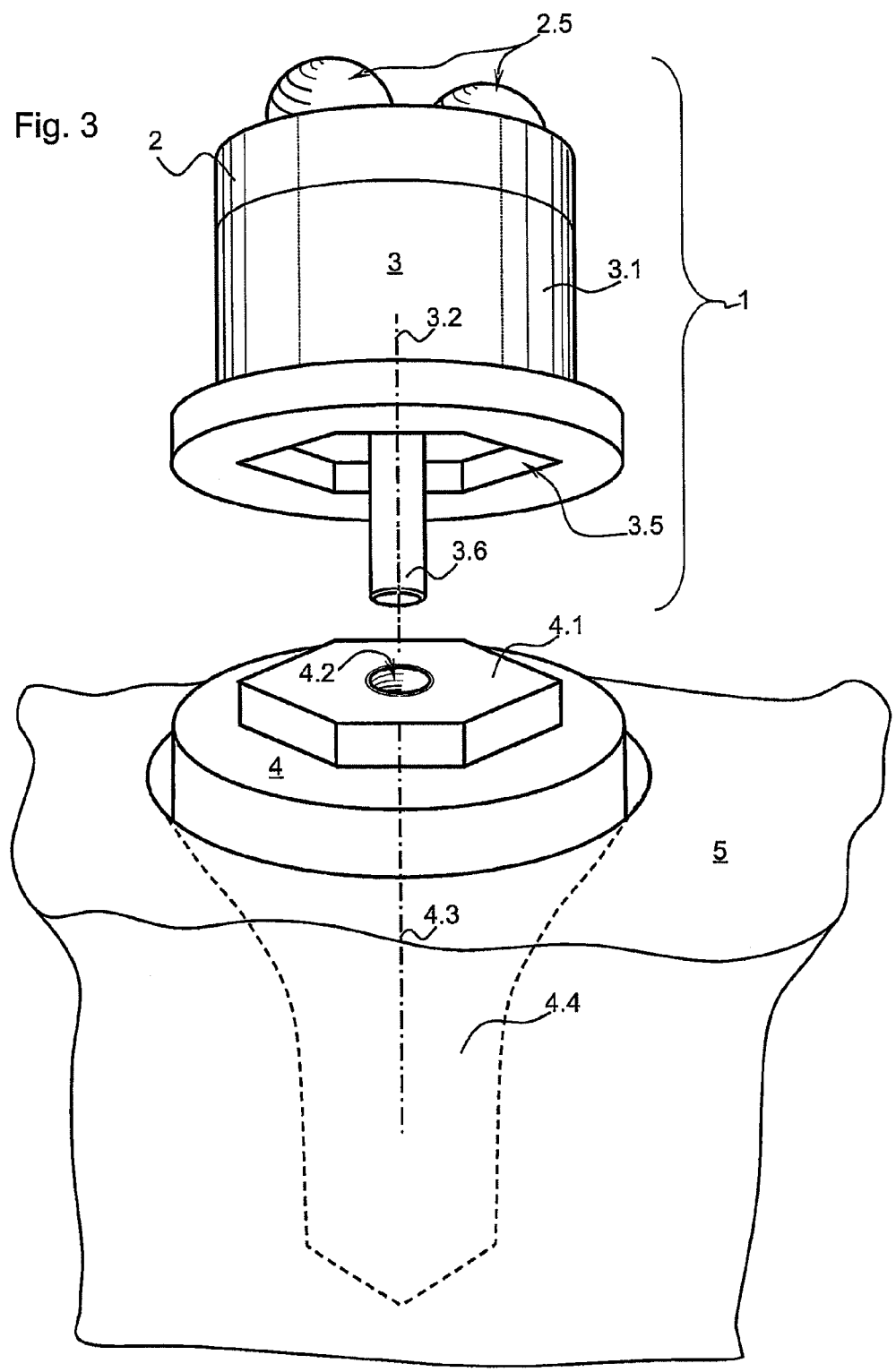
FIG. 3 is a perspective illustration of the measuring body and of the implant located in the jaw.

The supporting member 3 has, as shown in FIG. 3, on its side opposing the inspection part 2, a connecting geometry 3.5 which matches the connecting geometry 4.1 of the implant 4. The connecting geometry 3.5, 4.1 is in this case hexagonal, whilst the connecting geometry 3.5, 4.1 is in the form of a recess on the side of the supporting member and an eminence on the side of the implant.

The connecting geometry 3.5 also has a spigot 3.6, which can be inserted into a threaded bore 4.2 of the implant 4. The spigot 3.6 is coaxial with the longitudinal axis 3.2. In its inserted state inside the threaded bore 4.2, the spigot 3.6 is coaxial with the threaded bore 4.2 and thus coaxial with a longitudinal axis 4.3 of the implant 4. The axial alignment between the measuring body 1 and the implant 4 is effected mainly via the spigot 3.6 and the threaded bore 4.2, while the orientation in the vertical axial direction, i.e. relating to distance, and also the orientation in the circumferential direction are mainly achieved via the connecting geometries 3.5, 4.1 and their stop limit surfaces.

The implant 4 is screwed into the model of the jaw 5 via a threaded bore 4.4.

Figure 4:
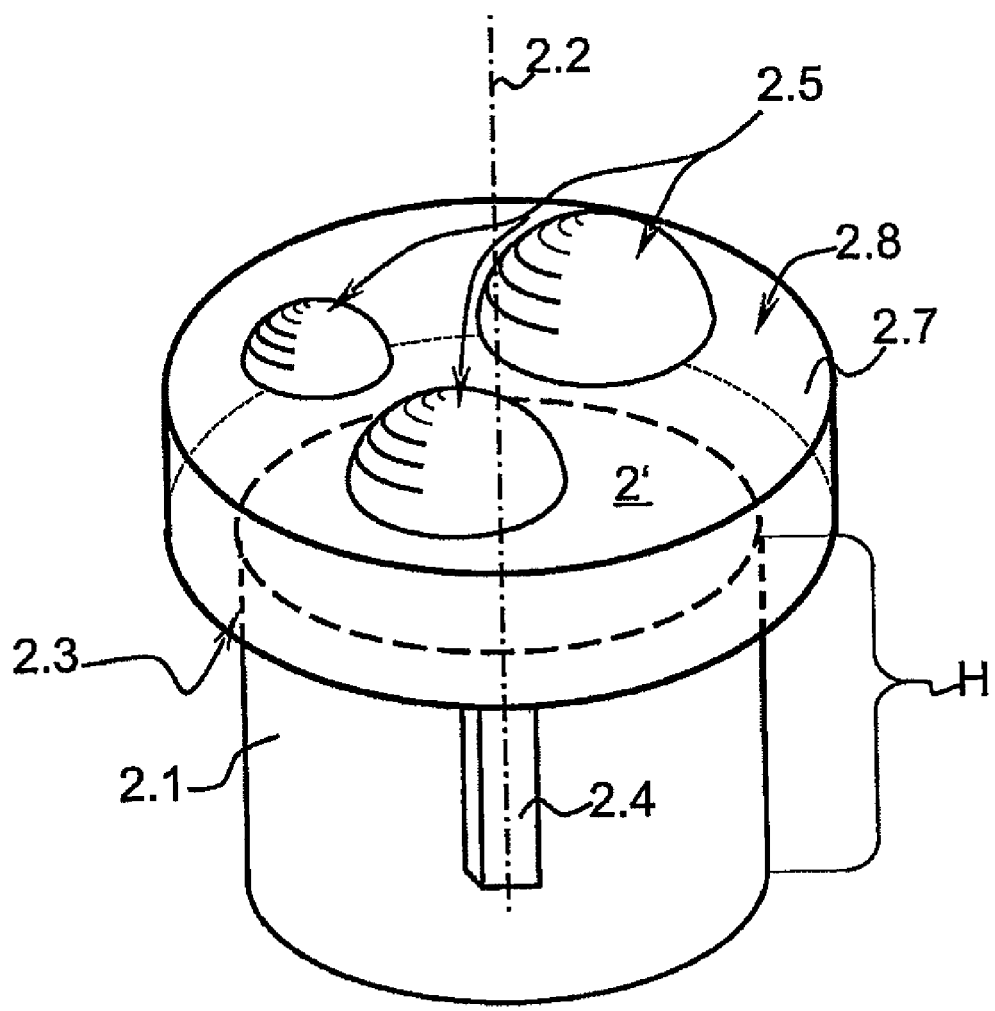
FIG. 4 shows an alternative inspection part.

The inspection part 2' illustrated in FIG. 4 can, like the inspection part 2 shown in FIG. 2, be attached to the supporting member 3 shown in FIG. 2. It has a similar measuring geometry 2.5, in which the three semispherical partial geometries are of different sizes, the differences relative to the inspection part 2 being sufficiently large, however, to make it possible to ascertain which of the two inspection parts 2, 2' is currently in use.

REFERENCE SIGNS 1 measuring body
2 inspection part, component
2' inspection part, component
2.1 counter-bearing, piston
2.2 longitudinal axis
2.3 second stop limit surface
2.4 orientation means, stop means, stop limit surface, tongue, projection
2.5 measuring geometry
2.6 free end
2.7 head
2.8 end face
3 supporting member, component
3.1 bearing, cylinder
3.2 longitudinal axis
3.3 first stop limit surface
3.4 orientation means, stop means, stop limit surfaces, groove
3.5 connecting geometry
3.6 spigot
4 implant
4.1 connecting geometry
4.2 threaded bore, groove
4.3 longitudinal axis
4.4 threaded bore
5 jaw
6 scanning camera
H height

What is claimed is:

1. A measuring body for an implant, comprising a measuring geometry detectable by a scanning camera and comprising a connecting geometry for said implant, wherein said measuring geometry is disposed on an inspection part and said connecting geometry is disposed on a supporting member, both of which form separate components, and said supporting member has a bearing for said inspection part and said inspection part has a counter-bearing for said bearing and said measuring geometry is provided at a free end of said inspection part, wherein said bearing and said counter-bearing have an orienting mechanism which ensures precise orientation between the supporting member and the inspection part in a circumferential direction relative to at least one of a longitudinal axis of said bearing and a longitudinal axis of said counter-bearing.

2. The measuring body as defined in claim 1, wherein said bearing has its longitudinal axis and a first stop limit surface effective in a direction of that longitudinal axis and said counter-bearing has its longitudinal axis and a second stop limit surface effective in a direction of that longitudinal axis, and said first stop limit surface and said second stop limit surface can be moved in an axial direction of the longitudinal axes so as to abut each other.

3. The measuring body as defined in claim 1, wherein said supporting member has a connecting geometry which matches the connecting geometry of said implant.

4. The measuring body as defined in claim 1, wherein said orienting mechanism is in the form of stop means or stop limit surfaces and form an anti-twist stop with reference to said longitudinal axes.

5. The measuring body as defined in claim 1, wherein said orienting mechanism of said bearing is in the form of a groove, and said mechanism of said counter-bearing is in the form of a projection, and said groove and said projection can be caused to abut each other in the circumferential direction to form an anti-twist stop.

6. The measuring body as defined in claim 1, wherein said bearing and said counter-bearing can be interplugged.

7. The measuring body as defined in claim 1, wherein said bearing is in the form of a cylinder and said counter-bearing is in the form of a piston.

8. The measuring body as defined in claim 1, wherein said connecting geometry has a spigot which can be pushed into a depression in said implant.

9. The measuring body for an implant, composed of the inspection part and the supporting member, wherein said inspection part and said supporting member are rigidly interconnected.

10. A method for generating a measured 3D image of a measuring body disposed on an implant wherein the implant to be used is selected from a number of various types of implants, the method comprising:
mounting a supporting member matching a type of the implant on said implant;
mounting a standardized inspection part structurally separate from said supporting member on said supporting member;
registering a measuring geometry of said inspection part, in mounted state, by means of a scanning camera,
the supporting member including a bearing for the inspection part and the inspection part including a counter-bearing for the bearing, the bearing and the counter-bearing including an orienting mechanism that ensures precise orientation between the supporting member and the inspection part in a circumferential direction relative to at least one of a longitudinal axis of the supporting member and a longitudinal axis of the inspection part, and the measuring geometry being provided at a free end of the inspection part.

11. A method for making a measured 3D image of a measuring body disposed on an implant the implant to be used being identified from a number of various types of implants, the method comprising:
connecting a standardized inspection part to a supporting member matching a type of the implant, the standardized inspection part fabricated separately from the supporting member;
mounting said measuring body on said implant by means of said supporting member,
registering a measuring geometry of said inspection part, in mounted state, by means of a scanning camera,
the supporting member including a bearing for the inspection part and the inspection part including a counter-bearing for the bearing, the bearing and the counter-bearing including an orienting mechanism that ensures precise orientation between the supporting member and the inspection part in a circumferential direction relative to at least one of a longitudinal axis of the supporting member and a longitudinal axis of the inspection part, and the measuring geometry being provided at a free end of the inspection part.

12. The method as defined in claim 11 or claim 11, wherein said inspection part is aligned with respect to said supporting member in the circumferential direction relatively to the longitudinal axis by means of the orienting mechanism.

13. The method as defined in claim 11, wherein said supporting member is aligned relatively to said implant in the circumferential direction with respect to at least one of the longitudinal axes by means of connecting geometries.

14. The method as defined in claim 11, wherein said bearing has a first stop limit surface and said counter-bearing has a second stop limit surface, the first and second stop limit surfaces are caused to bear abut each other in a direction of at least one of the longitudinal axes.

* * * * *